Figure 1:
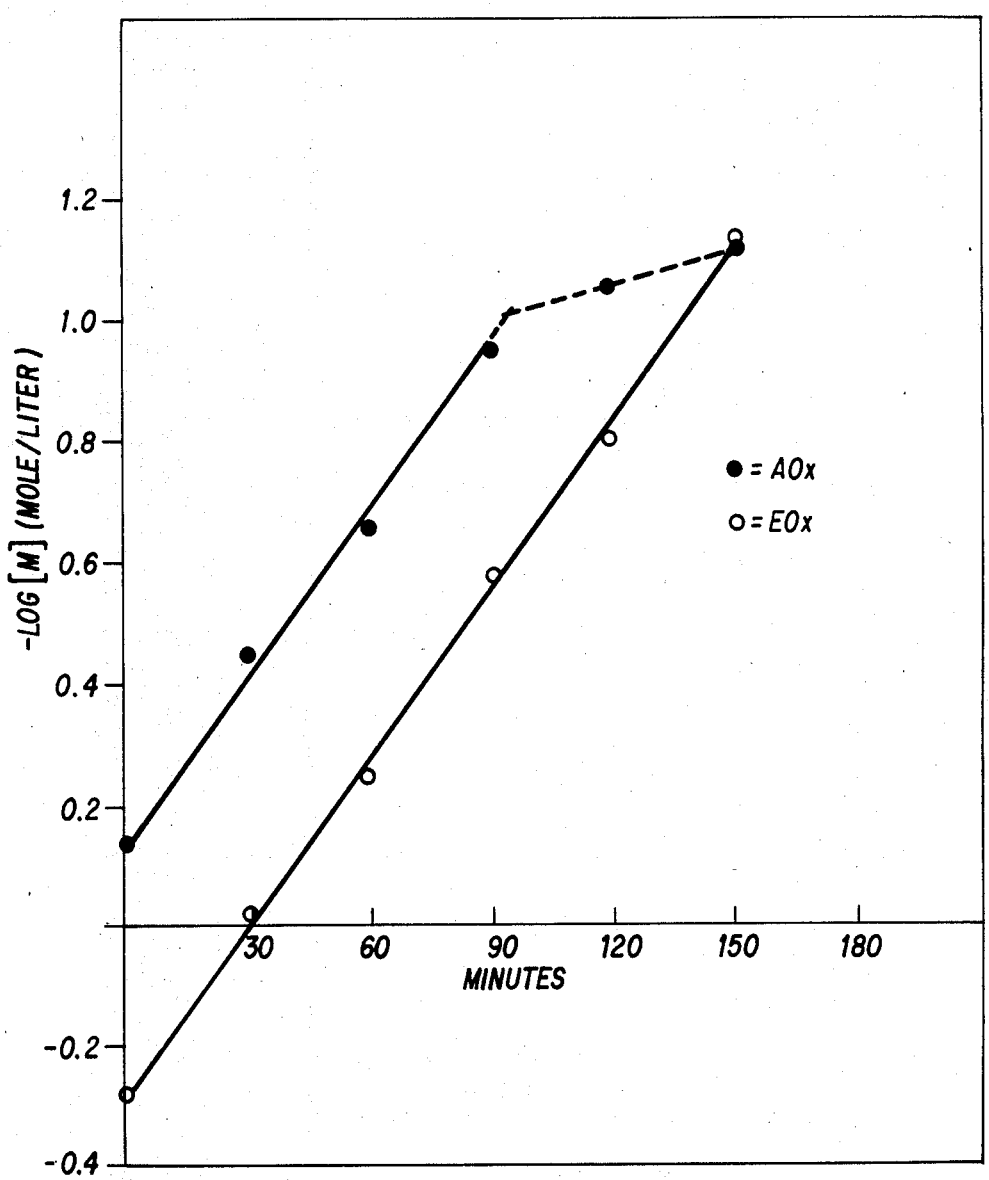

United States Patent [19]

Chou

[11] Patent Number: 4,709,039

[45] Date of Patent: Nov. 24, 1987

[54] VINYLOXAZOLINE MONOMER AND PREPARATION THEREOF

[75] Inventor: Richard T. Chou, Wilmington, Del.

[73] Assignee: The Dow Chemical Company, Midland, Mich.

[21] Appl. No.: 842,686

[22] Filed: Mar. 21, 1986

[51] Int. Cl.$^4$ .............................................. C07D 211/32
[52] U.S. Cl. .................................... 548/237; 548/215; 548/217; 548/238; 548/239; 526/260; 528/271; 528/423
[58] Field of Search ............... 548/237, 215, 217, 238, 548/239

[56] References Cited

U.S. PATENT DOCUMENTS

| | | | |
|---|---|---|---|
| 3,464,933 | 9/1969 | Levy et al. ............................. | 260/2 |
| 3,493,568 | 2/1970 | Levy et al. ............................. | 260/244 |
| 3,493,635 | 2/1970 | Davis et al. ............................ | 260/868 |
| 3,563,920 | 2/1971 | Tomalia et al. ........................ | 260/2 |
| 3,753,935 | 8/1973 | Miller ..................................... | 260/22 |
| 4,001,147 | 1/1977 | Chamberlin et al. .................. | 260/2.5 |
| 4,103,093 | 7/1978 | Lewis et al. ........................... | 560/205 |
| 4,247,671 | 1/1981 | Reitz et al. ............................ | 526/260 |
| 4,340,741 | 7/1982 | Vasta ..................................... | 548/237 |
| 4,357,464 | 11/1982 | Tomalia et al. ...................... | 548/237 |
| 4,368,309 | 1/1983 | Vasta ..................................... | 548/237 |

OTHER PUBLICATIONS

T. Saegusa, H. Ikeda, *Macromolecules*, 6, 805 (1973).
T. Saegusa, *Makromolecular Chemie*, 177, 2217 (1976).

*Primary Examiner*—Harold D. Anderson

[57] ABSTRACT

This invention relates to new organic compounds, including 2-(2-allyloxy-1-methylethyl)-2-oxazoline and 2-(vinylbenzyloxy-1-methylethyl)-2-oxazoline. Its method of preparation comprises condensing 2-(3-hydroxy-2-propyl)-2-oxazoline with allyl chloride and vinylbenzyl chloride, respectively, in a phase transfer process. The invention is also directed to a method of copolymerizing 2-ethyloxazoline with such compounds.

5 Claims, 3 Drawing Figures

VINYLOXAZOLINE MONOMER AND PREPARATION THEREOF

BACKGROUND OF THE INVENTION

1. Field of the Invention

This invention relates to vinyloxazoline monomers and copolymers and their preparation.

2. Background Art

This invention relates to new organic compounds, including 2-(2allyloxy-1-methylethyl)-2-oxazoline (AOx) and 2-(vinylbenzyloxy-1-methylethyl)-2-oxazoline (SOx). Its method of preparation comprises condensing 2-(3-hydroxy-2-propyl)-2-oxazoline with allyl chloride and vinylbenzyl chloride, respectively, in a phase transfer process. The invention is also directed to a method of copolymerizing 2-ethyloxazoline with such compounds. These monomers have an advantage over known 2-isopropenyl-oxazoline in their ability to be polymerized cationically without involvement of the vinyl groups and represent an improvement in the art over the following background references.

U.S. Pat. No. 3,563,920 relates to the ring-opening polymerization of bis-oxazoline compounds. The bis-oxazoline compounds contain sites of unsaturation.

U.S. Pat. No. 4,247,671 relates to vinyloxazolines which are polymerized through the vinyl group.

U.S. Pat. No. 4,103,093 relates to a polymer prepared from the copolymerization of an oxazolidinylethyl methacrylate, an alkyl methacrylate, and 2-hydroxyethyl oxazolidine.

U.S. Pat. No. 3,753,935 relates to a vinyloxazoline copolymer, wherein the oxazoline compound is polymerized through the vinyl group.

U.S. Pat. No. 3,464,933 relates to vinyloxazolines and copolymers derived therefrom.

U.S. Pat. No. 3,493,568 relates to polymers prepared by the ring-opening polymerization of hydroxyalkenyl oxazolines.

U.S. Pat. No. 3,493,635 relates to copolymers prepared from vinyloxazolines.

Poly oxazoline (POx) has been a material of considerable commercial interest. POx is useful in polymer additives. One of the most important physical properties of POx is its solubility. Thus, POx can be melt-blended with a number of thermoplastics (e.g, polyolefins, polyesters, saran, nylon). In addition, the excellent adhesive properties of POx may be utilized to improve adhesion of the thermoplastics to various substrates.

The synthesis of graft or block copolymers of POx is a logical approach to modify POx and maintain its bulk physical properties. The preparations of graft and block copolymers have been widely reported in literature. See T. Saegusa, H. Ikeda, *Macromolecules*, 6, 805 (1973); T. Saegusa, *Makromolecular Chemie*, 177, 2271 (1976), U.S. Pat. No. 4,001,147, both hereby incorporated by reference. Most approaches involve a polymer containing active halide groups or tosyslate groups (first stage) from where graft or block polymerizations (second stage) of oxazoline were conducted. This approach suffers low yield, slow polymerization rates, and generation of large amounts of Homo-POx. Furthermore, the preparation and purification (due to the nature of cationic polymerization of oxazoline) of "first stage" polymer is tedious and impractical. However, POx is prepared first and then in the presence of vinyl monomers, graft polymerizations are conducted by radical polymerization.

The present invention represents an improvement in the art, which will become evident to one having ordinary skill in the art on reading this entire specification, including the appended claims.

SUMMARY OF THE INVENTION

This invention relates to a monomer comprising:

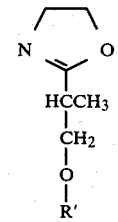

where R' being:

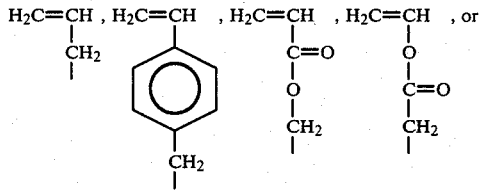

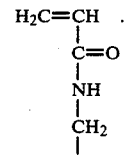

The invention further relates to a polymer comprising recurring units of the formula:

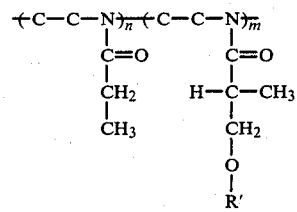

where R' being:

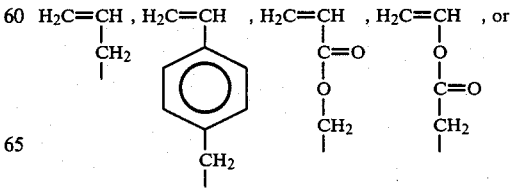

and m and n are integers greater than zero, representing degree of polymerization.

The invention also relates to a method for preparing vinyloxazoline of the formula:

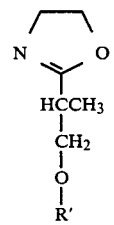

where R' being:

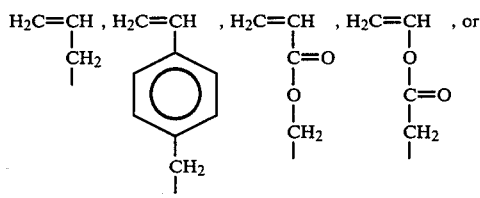

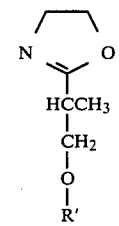

which comprises condensing 2-(3-hydroxy-2-propyl)-2-oxazoline with allyl chloride and vinylbenzyl chloride in the presence of a phase transfer catalyst, stron base and a solvent and recovering the monomer.

The invention further relates to a method of preparing a polymer having recurring units of the formula:

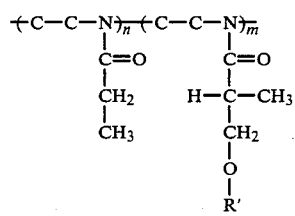

where R' being:

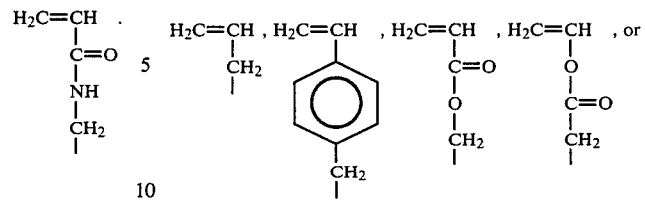

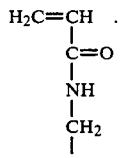

and m and n are integers greater than zero, representing degree of polymerization, comprising heating a monomer of the formula:

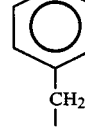

where R' =

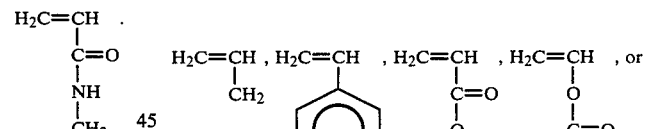

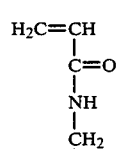

with a polymerization initiating amount of methyl p-toluenesulfonate (MeOTS) or methyl trifluoromethanesulfonate (MeTf).

EMBODIMENTS

The new monomeric compound is:

$$\begin{array}{c} \diagdown \\ N \quad O \\ \diagup \\ HCCH_3 \\ | \\ CH_2 \\ | \\ O \\ | \\ R' \end{array}$$

where R' =

$H_2C=CH$, $H_2C=CH$, $H_2C=CH$, $H_2C=CH$, or
$\quad\quad |\quad\quad\quad\quad |\quad\quad\quad\quad\quad |\quad\quad\quad\quad\quad |$
$\quad\quad CH_2\quad\quad\;\; \text{(phenyl-}CH_2\text{)}\quad C=O\quad\quad O$
$\quad\quad\quad\quad\quad\quad\quad\quad\quad\quad\quad\quad\quad\quad\quad |\quad\quad\quad\quad |$
$\quad\quad\quad\quad\quad\quad\quad\quad\quad\quad\quad\quad\quad\quad\quad O\quad\quad C=O$
$\quad\quad\quad\quad\quad\quad\quad\quad\quad\quad\quad\quad\quad\quad\quad |\quad\quad\quad\quad |$
$\quad\quad\quad\quad\quad\quad\quad\quad\quad\quad\quad\quad\quad\quad\quad CH_2\quad\;\; CH_2$ $H_2C=CH$
$\quad\quad |$
$\quad\quad C=O$
$\quad\quad |$
$\quad\quad NH$
$\quad\quad |$
$\quad\quad CH_2$ The new copolymers are of the type:

$$-(C-C-N)_n-(C-C-N)_m-$$
with side chains $C=O, CH_2, CH_3$ on one unit and $C=O, H-C-CH_3, CH_2, O, R'$ on the other.

where R' is the same as described above.

The utility of the monomer is that unique novel polymers, as shown above, can be prepared.

According to this invention, vinyloxazoline is prepared by Williamson ether formation utilizing 2-(3-hydroxy-2-propyl)-2-oxazoline as the key starting material. The general scheme of preparing novel vinyloxazoline and copolymers are shown below:

$$C=C(R_1)(R_2)Cl + N\diagdown O\diagup(R_3-OH) \xrightarrow[\text{solvent/aqueous (Base)}]{\text{phase transfer catalyst}} N\diagdown O\diagup R_3-O-C(R_2)=C(R_1)$$

where:
$R_1 = H, CH_3$; $R_2 = CH_2$, $R_3 = $ alkyl, phenyl-$CH_2$;

Phase transfer catalyst = $R_4NX$ (e.g., tetrabutylammonium hydrogen sulfate)

Organic solvent, such as a quaternary ammonium salt unreactive under the conditions of reaction such as tetrahydrofuran, dioxane, and the like Aqueous: NaOH (preferred 50%) in NaCl saturated $H_2O$ $$N\diagdown O\diagup(R_4) + C=C(R_1)(R_2-O-R_3) \xrightarrow{\text{cationic initiator}} -(C-C-N)_n-(C-C-N)_m-$$

where
$R_1$, $R_2$, and $R_3$ are the same as shown above.
$R_4 = $ alkyl
Cationic initiator =, for example, alkylation agents, such as arylsulfonate esters, e.g., methyl p-toluenesulfonate and methyl trifluoromethanesulfonate Preferred range of reaction conditions for the synthesis of vinyloxazoline are:

| Time | 3 to 10 hours |
|---|---|
| Temperature | 25° to 50° C. |
| Pressure | Atmospheric |

The preferred range of reaction conditions for the synthesis of copolymer are:

| Time | 1 to 24 hours |
|---|---|
| Temperature | 60° to 120° C. |
| Pressure | Atmospheric (preferred under $N_2$ gas) |

Further details about the process will be found in the Experimental section.

Poly(2-ethyloxazoline) (PEOx) is a valuable specialty polymer. The utility of the above copolymer is that this specialty polymer, with pendant vinyl groups, can undergo further polymerization, initiated by free radicals, for example, grafting or crosslinking. There is no known easy way or incorporate vinyl groups (or other reactive functional groups) into the polymer backbone. Poly(alkyloxazoline)-containing reactive vinyl groups can be utilized as a self-curing adhesive or as a compatibilizer in polymer blends, with the ability to be reacted with another polymer via pendant vinyl groups, and to improve the adhesion of thermoplastic polymers, such as polyolefins, polyesters and polyamides to various substrates.

Active vinyl groups can be incorporated into the PEOx backbone as a grafting site in the synthesis of graft copolymers. Thus, a vinyl monomer containing oxazoline rings has to be prepared. The requirements of this monomer are:

1. Containing no C=C—C=N bond (e.g., avoiding Michael reaction).
2. Containing no strong nucleophilic group except oxazoline ring.

The desired monomers can be readily prepared:

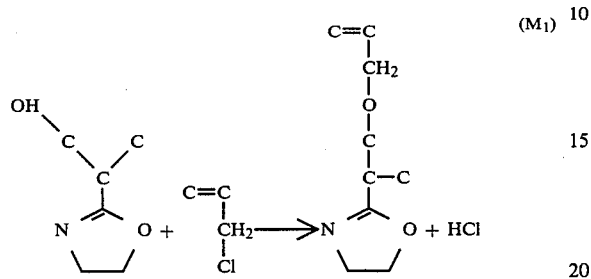
(M₁)

Thus, 2-ethyl-oxazoline and small amounts of M₁ may be copolymerized in the presence of the initiator like methyl tosylate. The vinyl group of M₁ should be under conventional polymerization conditions. The resulting polymer has the following structure.

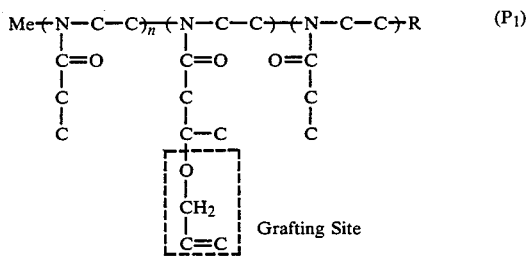
(P₁)

In the second stage, grafting polymerization of P₁ and vinyl monomers is induced by radical initiator. Due to the solubility characteristics of PEOx, a common solvent can be found so that the graft polymerization is carried out in a homogeneous condition. The degree of grafting can be controlled by different parameters, such as the concentration of M₁ in PEOx backbone, the P₁ and vinyl monomer ratio, and the concentration of radical initiator. The advantages of this procedure are: (1) essentially no Homo-PEOx generated, (2) grafting polymerization via a radical mechanism, (3) applicability to a variety of vinyl monomers. The obtained graft copolymers can be used in polyblend and adhesion.

The following compounds are within the scope of this invention:

Vinyloxazolines (1) 2-(2-allyloxy-1-methylethyl)-2-oxazoline (AOx)

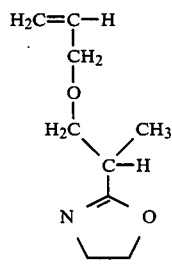

(2) 2-(vinylbenzyloxy-1-methylethyl)-2-oxazoline (SOx)

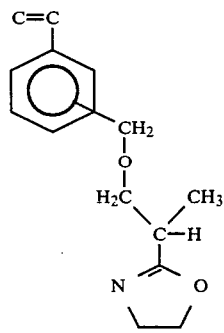

Copolymers of 2-ethyloxazoline and AOx

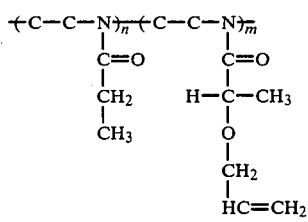

The following examples are given to further illustrate the invention, but it is to be understood that the invention is not to be limited by the details described therein. Certain explanations are presented. They are not intended to limit the present invention; however, they can assist in its understanding. In the examples, all percentages are by weight.

EXAMPLES

These experiments discuss the synthesis of novel vinyloxazolines and their copolymerizations with 2-ethyloxazoline. The objective of these experiments is to find a simple method to incorporate reactive vinyl groups into PEOx. A PEOx, with the ability to be cross-linked or to be chemically grafted onto another resin, is desirable in uses such as adhesives and polyblends. Novel vinyl oxazoline monomers, AOx and SOx, are prepared by condensing 2-(3-hydroxy-2-propyl)-oxazoline with allyl chloride and vinylbenzyl chloride, respectively, in a phase transfer process. This synthesis route, carried out at low temperatures but in the presence of a strong base, gives rise to over 90% conversion to products. But the thermal polymerization of SOx during distillation results in low yields of SOx. However, AOx can be easily isolated even in the absence of radical inhibitors. Copolymerization of EOx and SOx initiated by MeOTS leads to insoluble gel at about 4 mole % of SOx. Model studies concluded that crosslinking is caused by the side reaction of SOx during copolymerization, probably by thermal initiation of SOx. AOx, a thermally stable monomer, is proven a better candidate for copolymerization with EOx. Copolymers of EOx and AOx are obtained by using MeOTS or MeTf as initiators.

Monomer reactivity ratios $r_1 = 0.81$ and $r_2 = 0.33$ are obtained from kinetic studies of copolymerization of EOx (monomer 1) and AOx (monomer 2) initiated by MeTf. Because EOx has a larger monomer reactivity ratio than AOx, the monomer composition becomes richer in AOx with conversion. Two anomalous observations are found in copolymerization studies. First, MeOTS fails to initiate homopolymerization of AOx. Second, crosslinking reaction may occur in the homopolymerization of AOx or copolymerization with high content of AOx (50 mole fraction %) initiated by MeTf. In kinetic studies, copolymerizations of EOx and AOx (with 28 and 54 mole fraction %) resulted in soluble copolymers.

Chemicals

2-Ethyloxazoline, 2-(3-hydroxy-2-propyl)-2-oxazoline (HMEO), vinylbenzyl chloride (VBC), and divinylbenzene (DVB) are used. EOx is dried by 3 Å molecular sieve before use. Allyl chloride, methyl p-toluenesulfonate, and methyl trifluoromethanesulfonate are purchased from Aldrich Chemical Company. Tetrabutylammonium hydrogen sulfate, (t-Bu)$_4$NHSO$_4$, is obtained from Pfaltz and Bauer, Inc. Deuterated acetonitrile solvent is obtained from Norell, Inc. and Aldrich Chemical Company. Ethyl acetate and acetonitrile are dried by 3 Å molecular sieve before use as polymerization solvents.

Synthesis of Vinyloxazoline Monomers

The synthetic route to prepare vinyloxazolines is by condensation of 2-(3-hydroxy-2-propyl)-2-oxazoline HMEO with appropriate vinyl monomers. Several potential side reactions are possible in this synthetic approach: first, the dehydration of HMEO to 2-isopropenyloxazoline (IPO) in the presence of base or simply at high temperature; secondly, the thermal polymerization of the vinyl monomers; and thirdly, the electrophilic attack on oxazoline in the presence of acidic species.

A Williamson ether reaction facilitated by a phase transfer catalyst, (t-Bu)$_4$NHSO$_4$, is proven successful to synthesize vinyloxazolines. The synthesis scheme of 2-(2-allyloxy-1-methylethyl)-2-oxazoline and 2-(2-vinylbenzyloxy-1-methylethyl)-2-oxazoline are shown below:

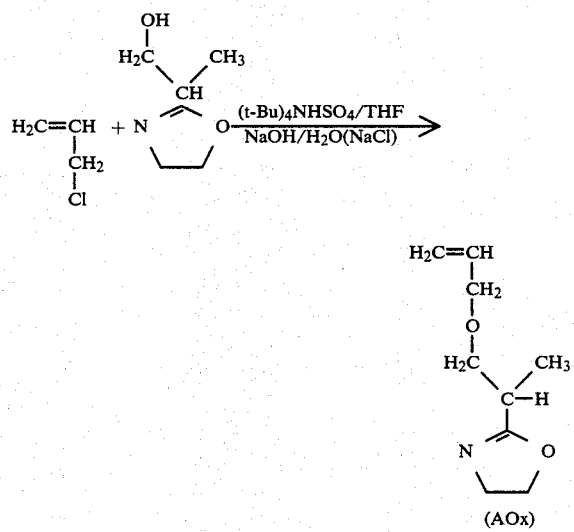

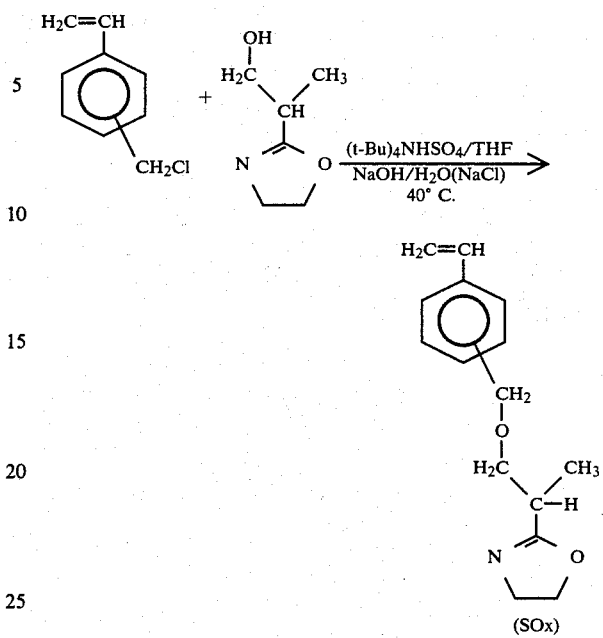

In this process, low reaction temperatures (35°–45° C.) but strong base (NaOH) are employed. The reaction is virtually completed in 3–4 hours. Under the reaction conditions described above, conversions of allylchloride or VBC based on GC analysis are above 90% in several runs. Except for the unreacted reactants, the potential side products are IPO from dehydration of HMEO and divinyl species resulting from the self-condensation of allyl chloride or VBC.

2-(2-Allyloxy-1-Methylethyl)-2-Oxazoline

In a three-neck round bottom flask, 24 g allylchloride (0.31 mole), 60 g 2-(3-hydroxy-2-propyl)-2-oxazoline (0.47 mole), 10 g of heptane, and 3.7 g (t-Bu)$_4$NHSO$_4$ phase transfer catalyst in 150 g tetrahydrofuran (THF) are added as the organic phase. The aqueous phase is 93 g NaOH solution prepared by dissolving 50 wt % NaOH into H$_2$O saturated with NaCl. The solution is agitated vigorously by a mechanical stirrer. Reaction is conducted at 40° C. for 3.5 hours. Conversion is over 90% according to GC analysis of crude product. After the reaction, the aqueous layer is decanted and the organic layer is extracted four times with H$_2$O saturated with NaCl. Tetrahydrofuran solvent is stripped off by a rotary evaporator. The remaining solution is filtered and dried over 3 Å molecular sieve. A pure monomer (99%) is obtained by distillation (0.12 mm/31° C.). The structure is identified by NMR and IR analysis.

2-(2-Vinylbenzyloxy-1-methylethyl)-2-oxazoline

In a three-neck round bottom flask, 45 g VBC (0.29 mole), 45 g HMEO (0.35 mole), 10 g heptane, and 4 g (t-Bu)$_4$NHSO$_4$ in 100 g THF solvent are added together as organic layers. 70 g NaOH aqueous solution prepared by dissolving 50 wt % of NaOH in H$_2$O saturated with NaCl is added as the aqueous layer. The reaction is carried out at 35°–45° C. for 4 hours. The reaction medium turned deep purple upon agitation. GC analysis of the crude product indicated over 90% conversion. The purification procedure is the same as described above. Due to the high boiling point of SOx, an Aldrich Kugelrohr apparatus is used to distill at a bath temperature of 150° C. under 2-3 mmHg pressure. The distillate is a colorless liquid. The structure is identified by GC and NMR analysis. Thermal polymerization occurs during distillation and results in a crosslinked gel in the distillation flask.

Gas Chromatography Analyses

Except for the kinetic studies, gas chromatography (GC) analyses are exclusively carried out by using a Hewlett-Packard analyzer equipped with a flame ionization detector and a 25 meter methyl silicone capillary column. In most cases, heptane is used as the standard.

In a typical example, the SOx reaction is analyzed by GC; the GC with pertinent peak assignments of the control (before reaction) and the product (before purification) samples are shown in Table 1.

TABLE 1

| GC Chromatographs of Control and Product Samples in Synthesis of SOx | |
|---|---|
| Retention Time (min) | Assignments |
| A. Control | |
| 2.04 | solvent |
| 2.24 | heptane |
| 3.39 | IPO |
| 4.82 | HMEO |
| 6.22 } 6.30 | VBC |
| B. Product | |
| 2.04 | solvent |
| 2.25 | heptane |
| 3.39 | IPO |
| 4.81 | HMEO |
| 11.01 } 11.16 | SOx |
| 11.45 } 11.61 } 12.21 } 12.44 | divinyl species |

IPO (peak 3.39) is detected in the reaction media (a) originating from HMEO (containing less than 2% IPO). After the reaction, the IPO concentration increased indicating the dehydration of HMEO by base. Because, in this process HMEO is used in excess amounts, the dehydration is inevitable, but negligible, compared to the major products. VBC exists in isomer form (p/m:60/40); the corresponding SOx (peaks 11.01, 11.16) is also formed in two isomer structures, even maintaining the same p/m ratio. Reaction is clean, and except for IPO, the possible side products are divinyl species with the structure shown below:

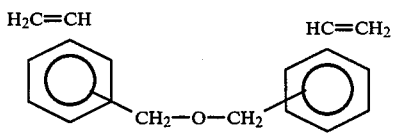

The divinyl species should exist in four isomer forms because of the self-condensation of VBC, as evidenced by the four small peaks at higher retention time regions. In order to suppress formation of the divinyl species, VBC is continuously added during the reaction for one run, which results in less divinyl species but only 75% conversion to SOx.

The isolation of SOx by distillation is a difficult task. The high boiling point and the tendency of thermal polymerization results in low yields. The addition of radical inhibitor, p-methoxyphenol, seems to suppress thermal polymerization to some extent. Purified SOx is a colorless liquid.

Similar results were observed in the synthesis of AOx. But compared to SOx, AOx is more easily isolated by distillation. No thermal polymerization is observed during distillation, even in the absence of a radical inhibitor. Purified AOx is a colorless liquid.

Copolymerization

Copolymerizations are carried out in glass ampoules one-half inch in diameter. After adding the appropriate reactants, the glass ampoules are sealed under vacuum. Polymerization is started by immersing the glass ampoules into an oil bath. The polymer is purified by dissolving in $CH_2Cl_2$ and precipitating in diethylether.

The kinetics of copolymerizations are carried out in a 5 ml vial. The vial is sealed by a Wheaton microvalve with a Teflon-faced silicone septum. The reaction is followed by taking samples with a 10 ml hypodermic syringe at different time intervals for GC analyses. The monomer concentrations are calculated by comparing the integral ratios of monomers to 1,2,4-trichlorobenzene.

Copolymerization of EOx and SOx

Copolymerizations of EOx and 1 to approximately 10 mole % of SOx (based on EOx) are carried out in ethyl acetate intitiated by $8.0 \times 10^{-2}$M MeOTS. The polymerization conditions and results are shown in Table 2. Copolymerizations result in soluble polymer in the presence of 1-3 mole % of SOx, but insoluble gel at higher SOx concentrations. The extraction of crosslinked gel (samples 4-6) failed to recover soluble PEOx, suggesting that the crosslinked structure contains both EOx and SOx monomers. The GC analysis of samples 4-6 (swelling in THF) indicated complete conversion of EOx and SOx.

TABLE 2

| Copolymerization* of EOx and SOx initiated by MeOTS | | | |
|---|---|---|---|
| Sample | SOx** (mole %) | EOx** (mole %) | Results |
| 1 | 1 | 99 | Soluble polymer |
| 2 | 2 | 98 | Soluble polymer |
| 3 | 3 | 97 | Soluble polymer |
| 4 | 4 | 96 | Insoluble gel |
| 5 | 5 | 95 | Insoluble gel |
| 6 | 10 | 90 | Insoluble gel |
| 7*** | 12 | 88 | No polymerization, 75% SOx recovered |

*Carried out in ethyl acetate solvent initiated by $8.0 \times 10^{-2}$ M MeOTS at 100° C. for 18 hours
**EOx concentration, 5.5 mole/liter, remains constant
***No MeOTS added In sample 7, EOx and 12 mole % of SOx are treated at the same heat condition in the absence of MeOTS. No copolymerization is observed. EOx is recovered quantitatively while only 75% of SOx is recovered, according to GC analysis. It is known that substituted styrene will undergo thermally initiated polymerization. Thus, 25% of SOx is probably consumed because of thermal initiation via styrenic groups. This information strongly suggests that the cause of crosslinking originates from the SOx comonomer.

Because the SOx used may contain small amounts of VBC and divinyl species (less than 5%), these compounds are also potential crosslinking agents. A model study is designed to eliminate this concern. Divinylbenzene (DVB) is used as a substitute for divinyl species. In the meantime, the possibility of adding polymerization inhibitors, p-benzoquinone and Ionol (2,6-di-t-butylphenol), to suppress the thermal initiation of SOx is another purpose of these model studies. One mole % of VBC or DVB based on EOx concentration is added into the EOx polymerization system, and it is initiated by 0.2 mol % of MeOTS. This VBC or DVB concentration range is the potential maximum contamination brought into the copolymerization system by 20 mole % SOx. The polymerization conditions and the results of GC analysis are shown in Table 3. The complete consumption of EOx in all polymerizations is confirmed by GC analysis. All samples are soluble polymers. About 13-30% of DVB (samples 1, 2, 3) is consumed; there is no apparent indication that radical inhibitor prevented the thermal initiation of DVB. But obviously, the small amount of DVB could not influence the cationic polymerization of EOx. The VBC is consumed completely, which is caused by the electrophilic attack of EOx by VBC. But, again, at such low concentrations, the presence of VBC does not present a problem for crosslinking.

TABLE 3

Model Studies: Polymerization* of EOx
In the Presence of Divinylbenzene or Vinylbenzyl Chloride

| Sample | Polymerization Conditions | | | % Conversion of Reactants**** | | |
|---|---|---|---|---|---|---|
| | DVB** mole % | VBC** mole % | Inhibitor | DVB | VBC | EOx |
| 1 | 1 | — | — | 15 | — | 100 |
| 2 | 1 | — | Ionol*** 2 mole % | 29 | — | 100 |
| 3 | 1 | — | p-benzo-quinone*** 2 mole % | 13 | — | 100 |
| 4 | — | 1 | — | — | 100 | 100 |
| 5 | — | 1 | Ionol*** 2 mole % | — | 100 | 100 |

*Carried out in ethyl acetate solvent initiated by 1.3 × 10$^{-2}$ M MeOTS at 100° C. for 16 hours
**Based on EOx, EOx concentration is 6.7 mole/liter
***2 mole % of inhibitor based on DVB or VBC concentration
****GC analysis of reaction mixture The above studies concluded that the crosslinking mechanism must be caused by the side reaction of SOx during copolymerization, most probably by thermal initiation of SOx. The presence of inhibitor may not have a dramatic effect on suppressing crosslinking during copolymerization of SOx and EOx. Thus, SOx is not a good candidate. Nevertheless, SOx is a novel vinyloxazoline monomer for radical polymerization.

Copolymerization of EOx and AOx

The stability of allyl-type monomers toward thermal polymerization led to preparation of allyl-type vinyloxazoline, AOx. A quantitative recovery of AOx is observed according to GC analysis by heating 2% AOx in ethyl acetate at 90° C. for 3 hours. Thus, AOx is an ideal comonomer for copolymerization with EOx.

Copolymerization of EOx and AOx Initiated by MeOTS

Copolymerization (Table 4) of EOx and AOx in different compositions is conducted in ethyl acetate initiated by MeOTS. In this case, as is expected, copolymerizations result in soluble polymers. The solubilities of these copolymers are slightly different from those of PEOx; they did not readily dissolve in H$_2$O. But the addition of 10% acetone brought the copolymers into solution. It is probably due to the existence of more hydrophobic AOx units. However, the homopolymerization of AOx initiated by 1 mole % of MeOTS failed; 96% of AOx is recovered according to GC analysis.

TABLE 4

Copolymerization* of EOx and AOx Initiated by MeOTS

| Sample | Mole % EOx | Mole % AOx | Polymerization Conditions | Results |
|---|---|---|---|---|
| 1 | 95 | 5 | 90° C., 2 hrs. | Soluble Polymer |
| 2 | 90 | 10 | 90° C., 2 hrs. | Soluble Polymer |
| 3 | 50 | 50 | 90° C., 3 hrs. | Soluble Polymer |
| 4 | 0 | 100 | 90° C., 4 hrs. | No Polymerization** |
| 5*** | 91 | 9 | 90° C., 3.5 hrs. | Soluble Polymer |

*Carried out in ethyl acetate solvent (50 volume %) initiated by 4.0 × 10$^{-4}$ M MeOTS
**According to GC analysis, 96% of AOx recovered
***Carried out in acetonitrile solvent Reaction between AOx and MeOTS (about 1:1 mole ratio) in CD$_3$CN is studied by NMR. The solution is heated at 60° C., and NMR spectrum is taken at 1 hour followed by 16 hour intervals. The methylation process can be followed by the new peaks generated at delta=3.33 (CH$_3$—N) and delta=2.33

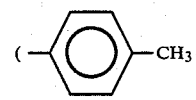

of reacted MeOTS). The rate of methylation is measured by the ratio of delta=2.33

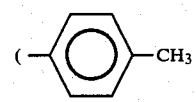

of reacted MeOTS) to delta=2.48

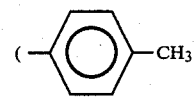

of unreacted MeOTS). MeOTS apparently is a very unreactive alkylation agent toward AOx. After 16 hours at 60° C., only 57% of the expected AOx salt is formed. However, the resulting N-methyl AOx salt is very stable. The NMR spectrum did not change, even after 5 days; the allyl group is intact, as evidenced from the unchanged integration ratio of vinyl protons.

Copolymerization of EOx and AOx Initiated by MeSO$_3$CF$_3$(MeTf)

A stronger alkylation agent, MeSO$_3$CF$_3$ is also used to initiate copolymerization of EOx and AOx. The results are shown in Table 5. At relatively low AOx concentration (Samples 1, 2), soluble polymers are obtained. At higher concentrations of AOx (Samples 3, 4), insoluble gels are obtained after polymerization. GC analysis indicated that only small amounts of AOx (less than 1%) remained, while EOx is completely consumed. Note that the reactivities of MeTf and MeOTS toward polymerization of AOx are quite different. One induced AOx homopolymerization; the other failed.

TABLE 5

Copolymerization* Of EOx and AOx Initiated by MeTf

| Sample | mole % EOx | AOx | MeTf* | Polymerization Conditions | Solvents** | Results |
|---|---|---|---|---|---|---|
| 1 | 91.5 | 8.5 | 8.5 | 90° C., 3 hours | CH$_3$CN | Soluble Polymer |
| 2 | 90.9 | 9.1 | 1 | 90° C., 3.5 hours | CH$_3$CN | Soluble Polymer |
| 3 | 50 | 50 | 1 | 90° C., 4 hours | Ethyl Acetate | Gel*** |
| 4 | 0 | 100 | 1 | 90° C., 4 hours | Ethyl Acetate | Gel*** |
| 5 | 0 | 100 | BF$_3$O(Et)$_2$ 1 mole % | 100° C., 4 hours | Ethyl Acetate | No Polymerization**** |

*Based on total monomer concentration
**50 volume % of solvent
***GC analysis indicated small amount of unreacted AOx
****IPO was detected In sample 5, BF$_3$O(Et)$_2$ is used to initiate polymerization of AOx. No polymerization is observed; detectable amounts of IPO are obtained. Probably AOx undergoes an ether cleavage induced by Lewis acid.

Being a "hotter" alkylation agent, MeTf readily reacts with EOx and AOx to form the corresponding n-methylated oxazoline salts, EOx-quat and AOx-quat, respectively. The reaction between the EOx-quat and AOx-quat with EOx would be the model reactions of the crossover processes during copolymerization, as shown below:

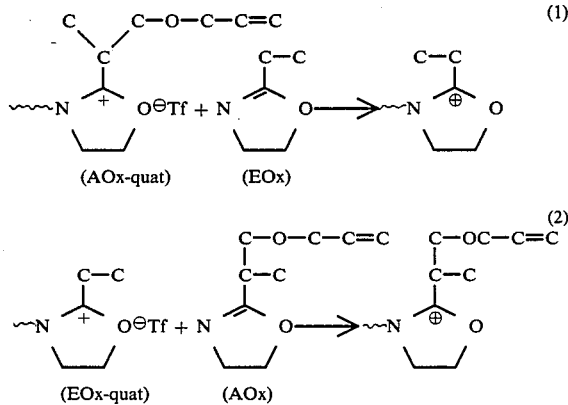

The AOx-quat is prepared by mixing about 1:1 mole ratio of MeTf and AOx in CD$_3$CN at room temperature. Exothermic heat indicated the rapid formation of AOx-quat. The solution is heated at 80° C. for 2 hours. The thermal stability of this salt is evidenced from the unchanged NMR spectrum. Then, 1 equivalent of EOx is added to the solution, and is heated at 80° C. for 2 hours. In spite of the complexity, inspection of spectra presents two interesting features. First, the methylene proton of EOx (delta=2.0-2.45 ppm), is shifted downfield (about delta=2.75 ppm), indicating the reaction (1) of EOx and AOx-quat. Secondly, the stability of allyl groups toward both heat and reaction (1) is confirmed from the inertness of vinyl protons (at about delta=5-.0-6.2 ppm).

The converse of the above reaction is carried out in the same manner. The NMR spectra are difficult to interpret due to the overlap of peaks. But nevertheless, the changes of peak patterns suggest reaction (2). Again, the inertness of the allyl groups during reaction is confirmed by peak integration.

In conclusion, model studies strongly suggest that the crossover reactions (1) and (2) occur during copolymerization, and that the allyl groups of AOx are stable under copolymerization conditions. It is interesting to point out the reaction between IPO-MeTf salt with EOx or the converse reaction always led to the disappearance of terminal vinyl groups. This is the basic difference between IPO- and AOx-type vinyloxazolines. Crosslinking reaction may occur in the homopolymerization of AOx or copolymerization with high content of AOx initiated by MeTf. In practical applications, a PEOx with a few mole percent of pendant allyl groups is suitable enough for further crosslinking or grafting reaction. However, this observation is not conclusive.

Kinetic Studies of Copolymerization of EOx and AOx

A kinetic study is worthwhile to further understand the copolymerization of EOx and AOx. Three reactions (Table 6) are carried out, in which mixtures of AOx and EOx are initiated by MeTf or MeOTS. The concentrations of AOx and EOx are followed by GC analysis, as shown in Table 7. 1,2,4-trichlorobenzene is used as the standard. Semilog plots of each monomer concentration vs. time are shown in FIG. 1 (run A), FIG. 2 (run B), and FIG. 3 (run C).

TABLE 6

Copolymerization* of EOx and AOx

| Run | EOx mole/liter | AOx mole/liter | Initiator mole/liter | T° C. ± 2 |
|---|---|---|---|---|
| A | 1.91 | 0.73 | MeTf 5.5 × 10$^{-2}$ | 85 |
| B | 1.07 | 1.23 | MeTf 6.1 × 10$^{-2}$ | 89 |
| C | 1.91 | 0.73 | MeOTS 6.8 × 10$^{-2}$ | 85 |

*Carried out in CH$_3$CN with 1,2,4-trichlorobenzene as the standard

TABLE 7

Kinetic Data of Copolymerization of EOx and AOx

| Time (Min) | Monomer Concentration | | Mole Fraction | | |
|---|---|---|---|---|---|
| | (EOx) mole/liter | (AOx) mole/liter | Polymer | EOx | AOx |
| Run A | | | | | |
| 0 | 1.910 | 0.734 | 0 | 0.720 | 0.28 |
| 30 | 0.888 | 0.360 | 0.53 | 0.34* | 0.14* |
| 60 | 0.566 | 0.221 | 0.70 | 0.21 | 0.08 |
| 90 | 0.275 | 0.112 | 0.85 | 0.10 | 0.04 |
| 120 | 0.158 | 0.089 | 0.91 | 0.06 | 0.034 |
| 150 | 0.073 | 0.075 | 0.94 | 0.028 | 0.028 |
| Run B | | | | | |
| 0 | 1.071 | 1.231 | — | 0.46 | 0.54 |

TABLE 7-continued
Kinetic Data of Copolymerization of EOx and AOx

| Time (Min) | Monomer Concentration | | Mole Fraction | | |
|---|---|---|---|---|---|
| | (EOx) mole/liter | (AOx) mole liter | Polymer | EOx | AOx |
| 18 | 0.624 | 0.852 | 0.36 | 0.27* | 0.37* |
| 27 | 0.413 | 0.632 | 0.55 | 0.18 | 0.27 |
| 38 | 0.282 | 0.487 | 0.67 | 0.12 | 0.21 |
| 58 | 0.123 | 0.372 | 0.78 | 0.05 | 0.16 |
| 78 | 0.054 | 0.274 | 0.86 | 0.02 | 0.12 |
| Run C | | | | | |
| 0 | 1.911 | 0.734 | — | 0.72 | 0.28 |
| 30 | 1.622 | 0.619 | 0.15 | 0.61 | 0.24 |
| 60 | 1.334 | 0.546 | 0.29 | 0.50 | 0.21 |
| 90 | 0.990 | 0.445 | 0.46 | 0.37 | 0.17 |
| 120 | 0.662 | 0.323 | 0.63 | 0.25 | 0.12 |
| 150 | 0.446 | 0.263 | 0.73 | 0.17 | 0.10 |

*As $M_1$ and $M_2$ values for determining $r_1$ and $r_2$ values

The monomer reactivity ratios $r_1$ and $r_2$ of EOx (monomer 1) and AOx (monomer 2) were calculated from a reformed Fineman-Ross equation.

$$r_1 = \frac{M_2^0 + M_2}{M_1^0 + M_1}\left[\frac{M_1^0 - M_1}{M_2^0 - M_2}\left(1 + r_2\frac{M_0^2 + M_2}{M_1^0 + M_1}\right) - 1\right] \quad (3)$$

where $M_1^0$, $M_2$ are the mole fractions of the monomers in the initial feed, $M_1$ and $M_2$ are the mole fractions of the monomers at a given time.

Figure 2:
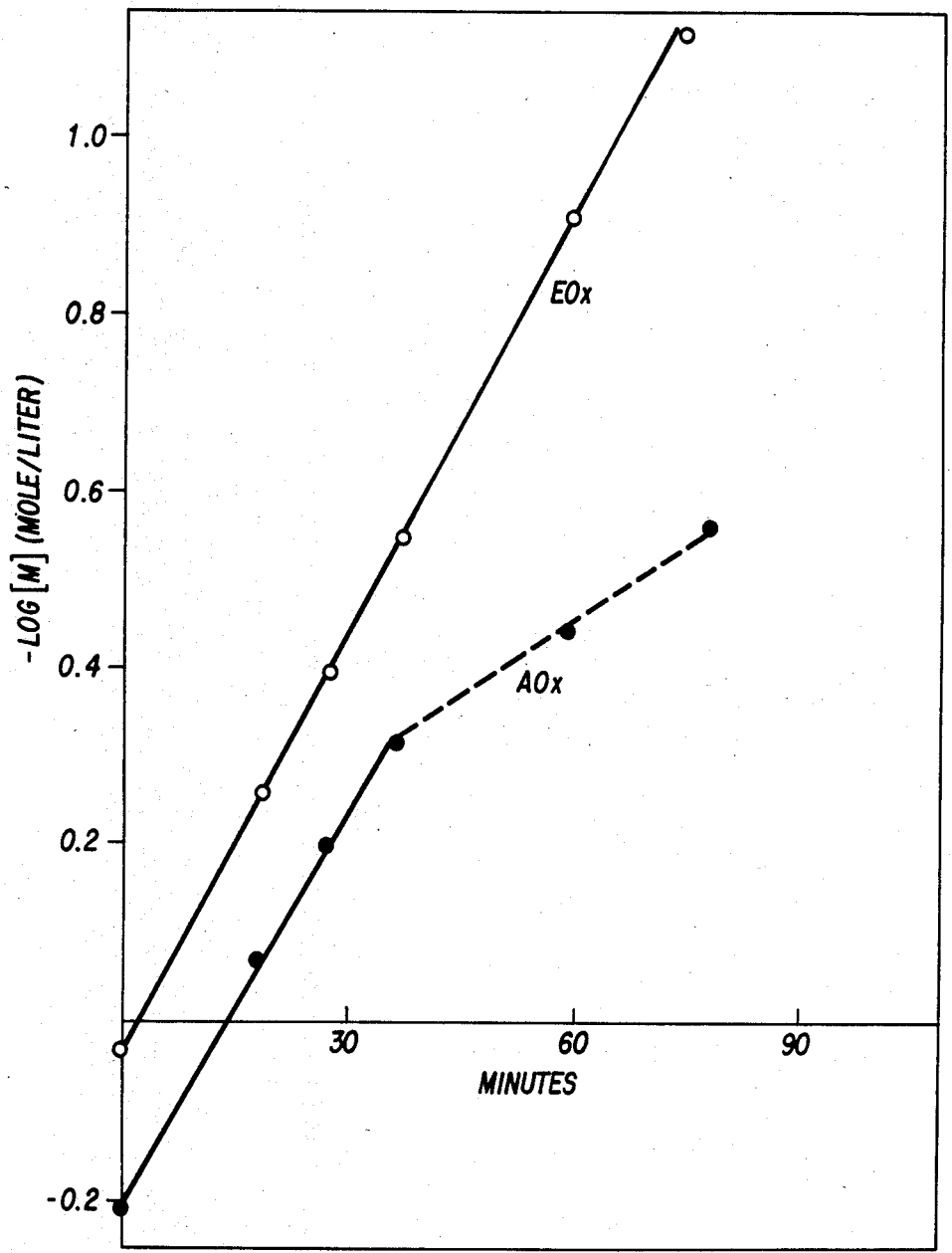

Two sets of data are selected from run A and run B by taking $M_1$ and $M_2$ values at the lowest conversions. $r_1 = 0.81$ and $r_2 32\ 0.33$ are obtained by solving the two linear equations of (3). Although run A and run B are carried out at slightly different temperatures, and the data points selected for $M_1$ and $M_2$ values are by no means from low conversions, this set of $r_1$ and $r_2$ values are in accordance with the results of copolymerizations. First, because EOx has a larger monomer reactivity ratio than AOx, the monomer composition should become richer in AOx with conversion. This agrees with the data (Table 7) of increasing AOx composition at high conversion regions in runs A and B. Secondly, with both $r_1$ and $r_2$ less than 1, a slight tendency toward alternating copolymerization is suggested. As shown in the accompanying drawings, which will make the nature of the present invention more readily apparent, FIGS. 1 and 2 show the consumption of AOx and EOx in a logarithm scale have similar rates, except at high conversion regions, implying the alternating copolymerization. But because of the great effect of gegenion on the monomer reactivity in cationic polymerization, the $r_1$ and $r_2$ values are not suitable to apply to other initiator systems, like MeOTS. As shown in Table 7, the polymerization rate of run A, initiated by MeTf, is much faster than of run C, initiated by MeOTS, under similar reaction conditions.

Figure 3:
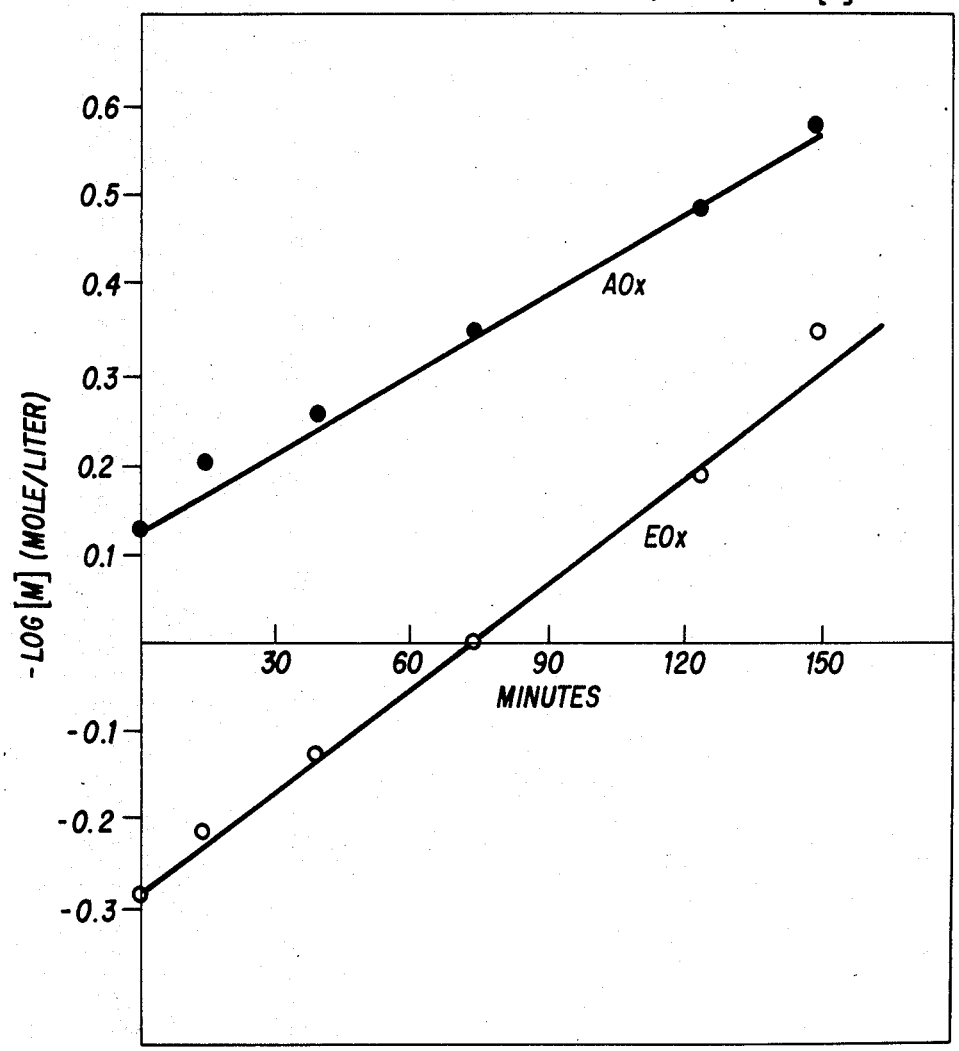

As shown in FIGS. 1, 2 and 3, each of the monomer participants seem to be reacting via first order pathways. But the consumption of AOx had a slower rate in the final stage of copolymerization. Run A and run B are carried out to complete conversions (greater than 99% based on GC analysis. In both samples, soluble copolymers are obtained. The integration ratios (%) indicate copolymer A containing 20 mole % of AOx and copolymer B containing 17 mole % of AOx. The copolymers have the general structure as shown below.

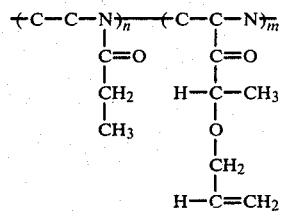

Two pertinent examples of graft copolymers are described below:

Graft Copolymers

Graft Copolymer PEOx-g-PS

Polystyrene (PS) and PEOx are an incompatible pair. Graft copolymer PEOx-g-PS is prepared, for example, by radical polymerization of styrene monomer in the presence of AOx containing PEOx copolymer. Accordingly, PEOx-g-PS copolymer may be used as an compatibilizing agent to promote adhesion between PS and another incompatible polymer (e.g. polyethylene (PE) which may be compatible with PEOx).

Graft Copolymer PEOx-g-PE

PEOx is incorporated under conventional conditions into a polyolefin like PE to promote adhesion with another material. PEOx ($P_1$) may be grafted onto PE in a twin screw reactor in the presence of radical initiator under conventional conditions.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A compound of the formula

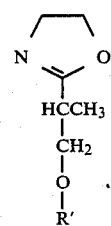

wherein R' is selected from the group consisting of:

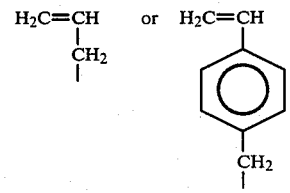

2. 2-(2-allyloxy-1-methylethyl)-2-oxazoline, a compound according to claim 1.

3. 2-(vinylbenzyloxy-1-methylethyl-2-oxazoline, a compound according to claim 1.

4. A method for preparing a vinyloxazoline of the formula:

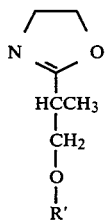

where R' being selected from the group consisting of:

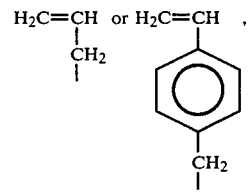

which comprises condensing 2-(3-hydroxy-2-propyl)-2-oxazoline with allyl chloride or vinylbenzyl chloride in the presence of a phase transfer catalyst, strong base and a solvent and recovering the vinyloxazoline.

5. A method according to claim 4, wherein the phase transfer catalyst is a quaternary ammonium salt.

* * * * *